(12) United States Patent
Fennell

(10) Patent No.: US 10,111,773 B2
(45) Date of Patent: Oct. 30, 2018

(54) METHOD AND APPARATUS FOR POSITIONING GAZE-ATTRACTING CONDOMS WITH PACKAGING

(71) Applicant: Keith Fennell, Raleigh, NC (US)

(72) Inventor: Keith Fennell, Raleigh, NC (US)

(*) Notice: Subject to any disclaimer, the term of this patent is extended or adjusted under 35 U.S.C. 154(b) by 327 days.

(21) Appl. No.: 14/971,894

(22) Filed: Dec. 16, 2015

(65) Prior Publication Data

US 2016/0166426 A1    Jun. 16, 2016

Related U.S. Application Data

(60) Provisional application No. 62/092,746, filed on Dec. 16, 2014.

(51) Int. Cl.
*A61F 6/00* (2006.01)
*B65D 23/12* (2006.01)
*B65D 25/20* (2006.01)

(52) U.S. Cl.
CPC .............. *A61F 6/005* (2013.01); *B65D 23/12* (2013.01); *B65D 25/20* (2013.01)

(58) Field of Classification Search
CPC .......... A61F 6/005; B65D 23/12; B65D 25/20
USPC ..................... 206/69; 224/901, 219
See application file for complete search history.

(56) References Cited

U.S. PATENT DOCUMENTS 5,460,188 A * 10/1995 Barrett, Sr. ............... A61F 6/04
                                                    128/842
5,551,612 A *  9/1996 Hochfeld ................ A61F 6/005
                                                    128/844

* cited by examiner

*Primary Examiner* — King M Chu
(74) *Attorney, Agent, or Firm* — Donn K. Harms

(57) ABSTRACT

A packaging system is provided for placement of condoms in a gaze-attracting position of a recipient of a gift or product. The system features a mount for holding the condom where the mount is adapted on one side to engage upon the product or the packaging surrounding it. Required removal of the mount to open the gift or positioning of the mount in a spot viewable after required sequential opening of the packaging insures the gaze of the recipient is captured and the location of the condom thereby ascertained.

15 Claims, 3 Drawing Sheets

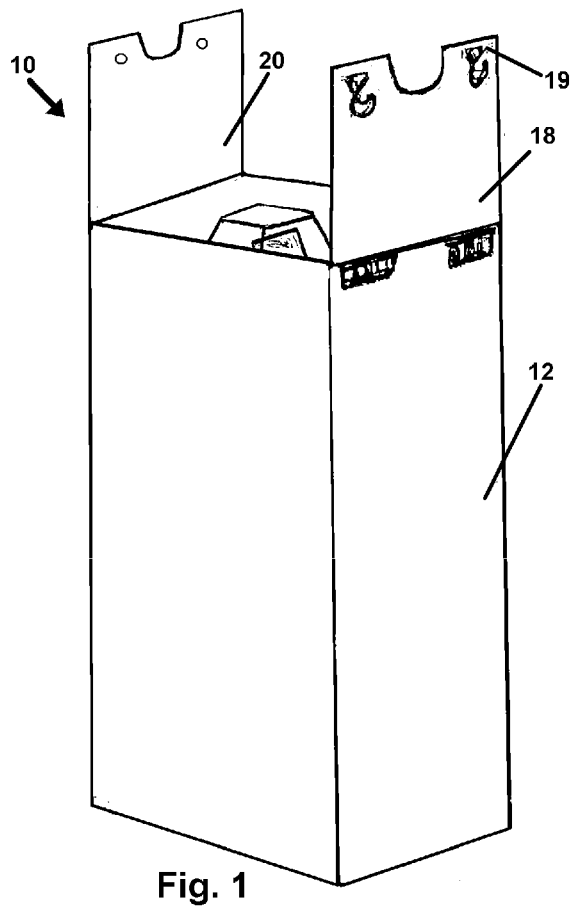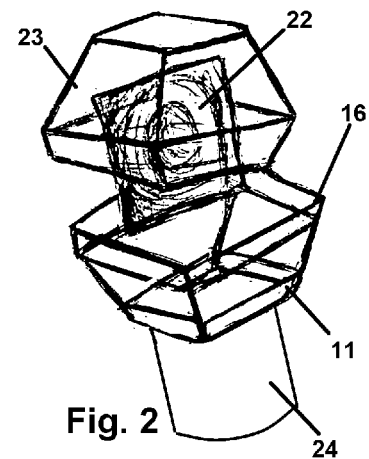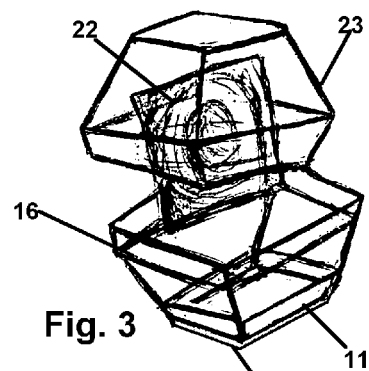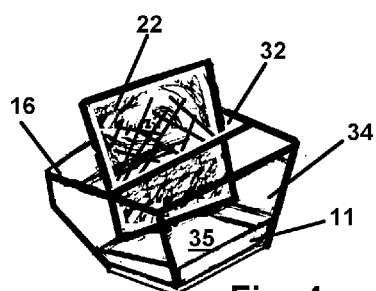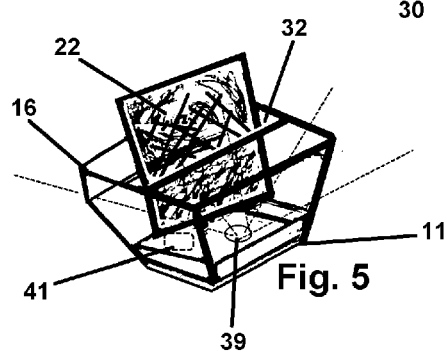
Fig. 1
Fig. 2
Fig. 3
Fig. 4
Fig. 5

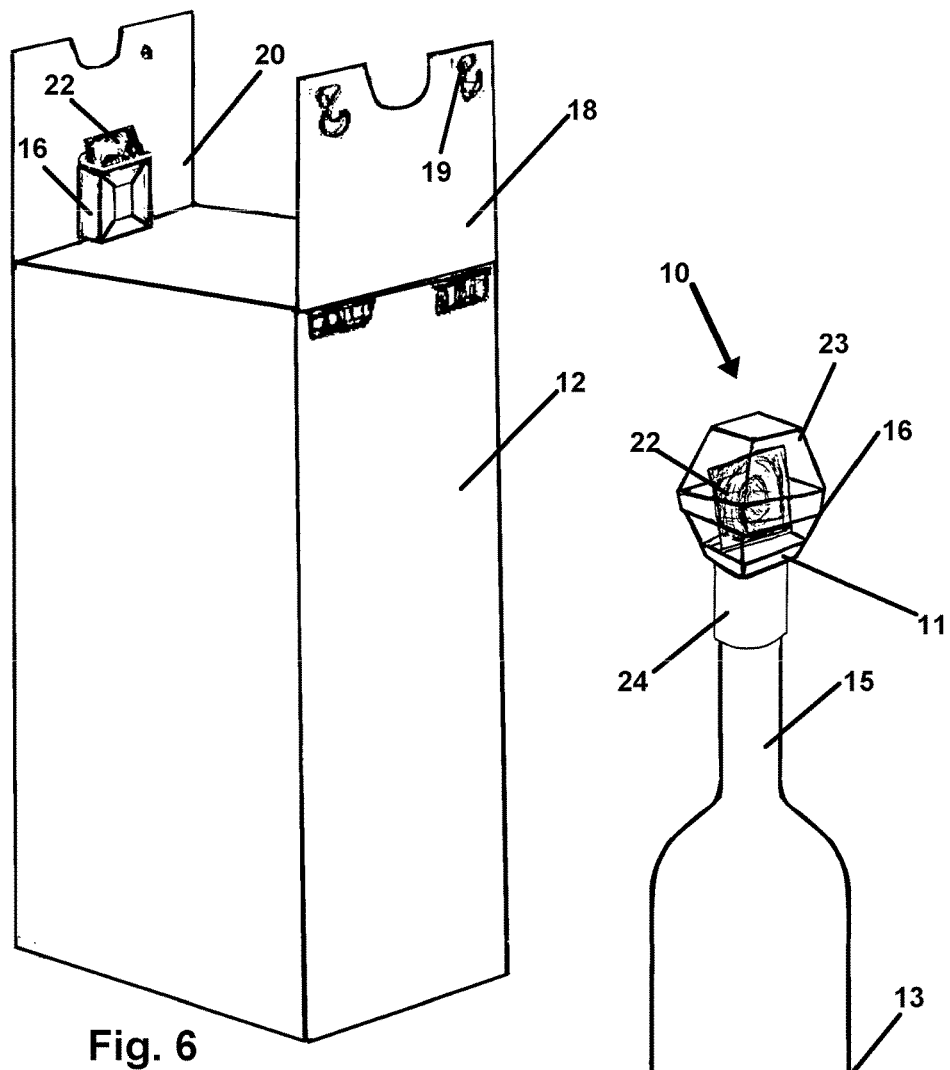

METHOD AND APPARATUS FOR POSITIONING GAZE-ATTRACTING CONDOMS WITH PACKAGING

This application claims priority to U.S. Provisional Patent Application Ser. No. 62/092,746 filed on Dec. 16, 2014, and incorporated herein in its entirety by this reference thereto.

BACKGROUND OF THE INVENTION

1. Field of the Invention

This invention relates to packaging of products. More particularly, it relates to a method and apparatus providing product packaging having highly visible storage and display component included therein, which is configured for receiving and retaining a packaged condom, and insuring discovery thereof by providing an attention-attracting positioning and packaging thereof.

2. Prior Art

Since the dawn of recorded history, presents such as food, candy, and alcoholic beverages have been something exchanged between people who are friends, and people who have evolved in a relationship to become more than just friends. On many occasions, such gift giving, especially on special holidays and celebratory days such as anniversary dates and birthdays, can precede the onset of sexual relations between the persons involved.

However, results of such activities can be hazardous to the health of the participants. Such can include the communication of sexually transmitted diseases such as AIDS and venereal diseases and the like, all of which are a tremendous problem in society. Further, even between monogamous couples, the outcome of an amorous evening can result in pregnancy. This is especially the case if subsequent to the receipt of a gift where the onset of intimate activity happens on the spur of the moment.

In the case of the exchange of gifts as noted above, frequently such gifts can include alcoholic beverages. Upon the ingesting of such gifts, even cautious people have been known to throw caution to the wind and indulge in intimate relations despite the previously known possibilities resulting from such.

As a prevention to unplanned pregnancy, and to help prevent the spread of sexually transmitted diseases, government, physicians, and sexual educators have long promoted the use of condoms during sexual activity. Such condom use has been shown to be a substantial preventive measure to avoiding unwanted pregnancy, and especially for preventing transmission of many sexually transmitted diseases.

However, the onset of sexual activities being hard to predict, especially where the ingestion of alcoholic beverages is involved, many participants initiating such activities find themselves unprepared because of the lack of a condom in the proximity to ongoing and increasingly heated activity.

In such moments, many participants find it, at best, inconvenient to cease such activity to seek out and find a condom. Further, in some cases, the intimate activity may be intentional on the gift-giver's part, but previously unknown to the recipient who may be unprepared for the subsequent physical activity. Therefore, lacking a condom proximate to their activity, especially after ingesting alcoholic beverages, many potential participants in sexual activities, choose to risk the outcome of failing to employ a condom.

As such, in the case of gift giving, especially where the gift is planned as an inducement to subsequent sexual relations, and particularly where the gift might be an alcoholic beverage, there is an unmet need to provide access to a condom, which can be quickly accessed should such plans succeed. Such a provision of a condom should preferably be provided in an engagement to the gift product itself, or alternatively in a highly visible manner on the gift packaging to be opened. Further, such a provision of a condom should be provided in a tasteful manner, and also should provide such packaging or product attachment or a container for the condom, which is positioned and/or illuminated or otherwise provided with a means to attract the gaze and the immediate attention of the parties opening the package as to the presence and the proximity of the condom, should it become necessary to seek to employ it for its intended purpose.

SUMMARY OF THE INVENTION

The system herein of combining a condom having a housing or container engageable with a product or with packaging for a product as herein disclosed and described, provides the remedy for the shortcomings of prior art.

As shown in the drawings and described in the detailed specification, the system herein provides a mount or container specifically adapted for positioning of a condom therein, which may be engaged either with a package of a product in one mode, or the product itself in another mode. The container or attachment is configured to hold and display a condom in a fashion where it comes to the visual attention of the person or persons receiving the product or package, and attracts the gaze of the recipient. The mount is configured to securely hold the condom but to also provide high visibility of its presence and positioning on the mount whether attached to the packaging or the product itself.

In one mode, the mount is adapted to engage the dispensing end of a bottle holding an ingestable liquid such as alcoholic beverages, for instance, wine or champagne. The mount is configured for a bottle engagement on a first end employing a bottle-engaging sleeve projecting from a first end surface of the condom-holding mount. When engaged to an as-used position with the sleeve in engagement with and surrounding the dispensing end of the bottle, the condom is positioned in the mount and rendered highly visible and adapted to attract the gaze of the recipient or user. Should the user initially visually miss the presence of the condom and mount, when access to the liquid in the bottle is subsequently attempted, their attention will again be drawn to the mount and condom since the dispensing end of the bottle is covered by the sleeve on the first end. Since the user must remove the mount, condom, and sleeve to imbibe in the contents of the bottle, they will certainly become aware of the presence of the mount, as well as the presence of the condom engaged with the mount when they remove it.

In another mode, the mount is adapted for engagement to the package enclosing the product, gift, or bottle. In this mode, adhesive is employed to mount on an internal or external surface of the packaging. The package itself is configured such that one end panel must be opened before a second end panel is opened to provide access to the bottle or present in an interior cavity. This forced sequential opening helps attract the gaze of the user to the mount when the end panels are opened, thus disclosing the presence of the mount and condom when opened.

To significantly enhance the gaze-attraction of the gift recipient, in addition to locating the mount to block access to the contents of the bottle, or on a sequentially opened flap, all modes of the device and method herein can also include a visual or audible alert which will generate sound or illuminate, or both, upon opening of the container. Such can be enabled by an illumination component such as an LED, a small loudspeaker, a light sensor, and/or motion switch, which will connect onboard power to cause the LED to illuminate, and/or the loudspeaker to play sound such as music which is held in electronic memory on the device, or both. Thus, upon opening the container, light reaching the light sensor or movement communicated to the motion switch, will initiate the sound and/or illumination of the mount and its contents to insure the gaze of the recipient user is attracted. The LED can be configured to direct light emitted, directly upon the condom if such is desired to significantly enhance the alert to its presence and/or it can be configured to emit light through a formed aperture in the box or container to attract the gaze of the recipient before and during opening of the package.

With respect to the above description, before explaining at least one preferred embodiment of the condom and packaging of the herein disclosed invention in detail, it is to be understood that the invention is not limited in its application to the details of the method herein and to the arrangement of the steps or configurations in the following description or illustrated in the drawings. The invention herein described is capable of other embodiments and of being practiced and carried out in various ways which will be obvious to those skilled in the art upon reading and being educated by this application. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other condom presentation mounts and methods and systems for carrying out the several purposes of the present disclosed system herein. It is important, therefore, that the claims be regarded as including such equivalent construction and methodology insofar as they do not depart from the spirit and scope of the present invention.

It is an object of the invention to provide a mount for a condom which is adapted for highly visible engagement on a product or on a package for a product to thereby attract the gaze of the recipient.

It is an object of the invention to provide such a mount and presentation of a condom, which does so in a manner to gain the immediate attention of a person opening the product or packaging for the product.

It is a further object of this invention, to provide a mount for a condom which prevents access to liquid in a bottle without removing the mount first.

These and other object features, and advantages of the present invention, as well as the advantages thereof over existing prior art, which will become apparent from the description to follow, are accomplished by the improvements described in this specification and hereinafter described in the following detailed description which fully discloses the invention, but should not be considered as placing limitations thereon.

BRIEF DESCRIPTION OF DRAWING FIGURES

FIG. 1 depicts a perspective view of the device engaged to one end of a packaged bottle or product in a position to render it immediately visible upon opening the package.

FIG. 2 is a depiction of the device configured on a first side with a bottle engaging sleeve projecting therefrom, and configured on a second side for operative removable engagement of a condom.

FIG. 3 shows the device having an adhesive engagement allowing for positioning on or in a package as in FIGS. 6-7.

FIG. 4 shows the device including a mount having a slot sized for sliding engagement of the condom so that a portion thereof projects therefrom for easy grasping if needed.

FIG. 5 depicts a mode of the device having illumination and/or sound components engaged to emit sound and/or light powered by an onboard power, to provide gaze-attraction to gain the attention of a person as to the presence of the mount and the condom engaged therewith.

FIG. 6 depicts the mount device holding a condom and adhesively engaged to an openable flap of product packaging where it will be noticed during opening of the package.

FIG. 7 depicts the device as in FIG. 2, showing the sliding or frictional engagement on the dispensing end of a bottle to require removal prior to dispensing liquid from the bottle.

Figure 8:
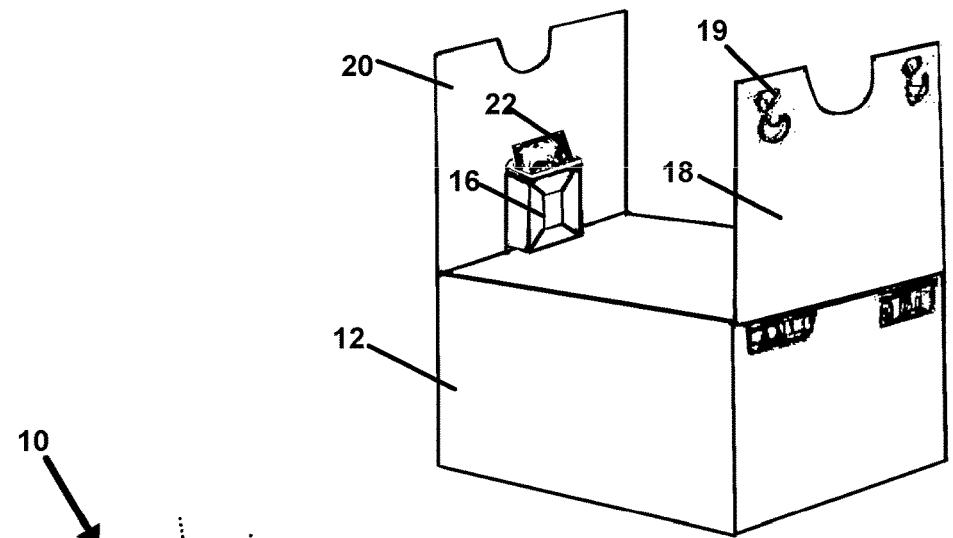
FIG. 8 depicts the device as in FIG. 6 but showing the package adapted to house products such as candy, jewelry, or flowers, or the like with the device positioned in a gaze-attracting position.

Other aspects of the present invention shall be more readily understood when considered in conjunction with the accompanying drawings, and the following detailed description, neither of which should be considered limiting.

DETAILED DESCRIPTION OF THE PREFERRED EMBODIMENTS OF THE INVENTION

In this description, the directional prepositions of up, upwardly, down, downwardly, front, back, top, upper, bottom, lower, left, right and other such terms refer to the device as it is oriented and appears in the drawings and are used for convenience only. Such terms are not intended to be limiting or to imply that the device has to be used or positioned in any particular orientation.

Now referring to drawings of FIGS. 1-9, wherein similar components are identified by like reference numerals, there is seen, in FIG. 1, a perspective view of one mode of the device 10 having a body 11 forming a mount 16 which is positioned in an as-used position, engaged with a product such as a bottle 13 (FIG. 7). If with a bottle 13, the mount 16 is preferably adapted on a first side of the body 11 of the mount 16, to engage upon the dispensing end 15 of the bottle 13, wherein an opening of the surrounding container 12 by sequential opening of a first end 18 overlapping a second end 20, will immediately focus the gaze or attention of the recipient, on the mount 16 and condom 22 therein.

Further, when engaged to a bottle, even after opening the container 12 if employed, opening the dispensing end 15 of the bottle 13 will require removal of the body 11 forming base of the mount 16, and further focus the gaze and attention of the recipient, on the device mount 16 and its contents which in a preferred mode, is a condom 22 for which the body 11 is adapted to removably engage.

In a favored mode, such may be accomplished by selling the engaging mount 16, in a combination with a container 12 surrounding the bottle 13 or product, where the container 12 has sequentially openable flaps or ends 18 and 20. The ends 18 and 20 can be configured where a first of the ends 18, must engage over the top surface of the second end 20, because the mating fasteners 19 and 21 require such, and thus the first end 18 must be opened first. Forming the ends to cause and overlap 31 (FIG. 9) is particularly preferred in all modes where the container is provided, to force the recipient to open the container 12 in a particular order. This is accomplished by forming the first end 18 slightly longer than the second end 20, to cause the overlay 31 and the first end 18 to lay slightly on top an overlay 31 area of the distal edge of the second end 20. Thus, the recipient must release the fasteners and open the first end 18 first, and the second end 20 subsequently, since it is overlain by the first end 18. Mating fasteners such as hook and loop fabric, snaps, magnets, or the shown rotatable hooks 19 which engage posts 21 (FIG. 9) can also be used. The mating fasteners are attached preferably such that the first end 18 only engages to the second end 20 to form the overlay 31. This can be done using hooks 19 which engage posts 21 on the second end 20, or snaps, hook and loop, or other mating fasteners on the facing surface of the first end 18 which overlays the facing surface of the second end 20. This configuration which requires the recipient to only open the container 12 in one sequence thus will cause the recipient to view under the second end 20 as it is opened since the first end 18 will generally block their view.

Upon opening the second end 20, the product-engaged mount 16 with no lid or a transparent lid 23, places the condom 22 engaged with the body 11, into the immediate view and attention of the recipient.

Shown in FIG. 2 is a depiction of the mount 16 having a condom engaging body 11 and which may have a transparent cap 23 as shown disengaged from the body 11. On a first side of the body 11 a sleeve 24 adapted in diameter to frictionally engage the dispensing end 15 of a bottle 13, projects. The sleeve 24 is preferably sufficiently elastic to allow it to stretch and contract and achieve a compressed engagement on the dispensing end 15 of a plurality of bottles 13 having different diameters at the dispensing end 15.

Such an engagement, as best shown in FIG. 7, places the sleeve 24 in a frictional and compressed engagement around the dispensing end 15 of the bottle. This also places the condom 22 engaged with the body 11 such as in a slot 32, and positioned in full view at the dispensing end 15 of a bottle 13 of liquid, for instance, liquor, wine, or perfume. In this mode, the recipient is prevented from access to the liquid contents of the bottle 13 until they have removed the sleeve 24 and body 11 of the mount 16 which of course will provide a means to focus their attention on the proximity and easy access to the condom 22.

In FIG. 3 another mode of the mount 16 is shown. In this mode, the first side of the body 11 includes an adhesive attachment 30 which allows for a positioning thereof on a surface of, or within, the product container 12 or packaging as depicted in FIGS. 6 and 8 for example. Again, the containers 12 should be configured with sequentially opening first ends 18 and second ends 20, so as to have the recipient open the first end 18 first, and place the body 11 of the mount 16, directly in view along with the condom 22 therein, as in FIG. 6 or FIG. 8.

FIG. 4 depicts the body 11 of the mount 16 having a slot 32 communicating into a cavity 34. The slot 32 is positioned a distance away from the bottom surface 35 of the cavity 34 defined by a sidewall 37 surrounding the bottom surface 35. The distance of the slot 32 from the bottom surface 35 on which the condom 22 will rest when inserted into the slot 32, is less than the distance across the package of the condom 22. Thus, a condom 22 engaged through the slot 32, in this mode, will have a grasping area 22a of the condom 22 package, projecting above the slot 32, thereby defining a portion of the condom 22 in the area above the slot 32, which provides an easy means for grasping and removing the condom 22 should such be desired.

In FIG. 5 is shown a mode of the device wherein the body 11 of the mount 16, includes one or both of a light emitter such as an LED 36 and sound emitter such as a loudspeaker 41 operatively engaged with the body 11 of the mount 16. The current favored means for illumination is an LED 36 powered by an onboard battery (not shown). Sound can be communicated from the speaker 41 positioned on body 11 of the mount 16 which is generated from digital files in onboard digital memory and an amplifier (not shown but well known) to play the sound through the loud speaker 41. Thus, the recipient is provided with visual and/or audible means with which to attract the gaze and thereby gain the attention of the recipient as to the presence of the mount 16 and the condom 22 engaged therewith.

FIG. 6 and depict the mount 16 having the body 11 holding a condom 22 engaged therewith, such as in a slot 32 as in FIG. 4. The mount 16 is engaged to the bottom of the second flap 20 of product packaging or container 12, such that it will immediately be noticed during opening of the sequential opening of the flaps of the container 12 for the held product such as alcohol, wine, perfume, flowers, or other packaged goods.

FIG. 7 shows the device 10 formed to the mount 16 is formed by the body 11 and can include a lid 23 such as shown in FIG. 2, and also depicting the frictional engagement of the elastic or flexible sleeve 24 on the dispensing end 15 of a bottle 13 used for liquid. In this mode, the container 12 such as shown in FIG. 1, would be optional. Of course this mode is particularly favored with or without the container 12 as it requires the recipient to view, and remove the mount 16 with its condom 22 contents prior to dispensing liquid from the bottle 13 and particularly attracting the gaze and attention of the recipient as to the presence and contents of the mount 16.

Figure 9:
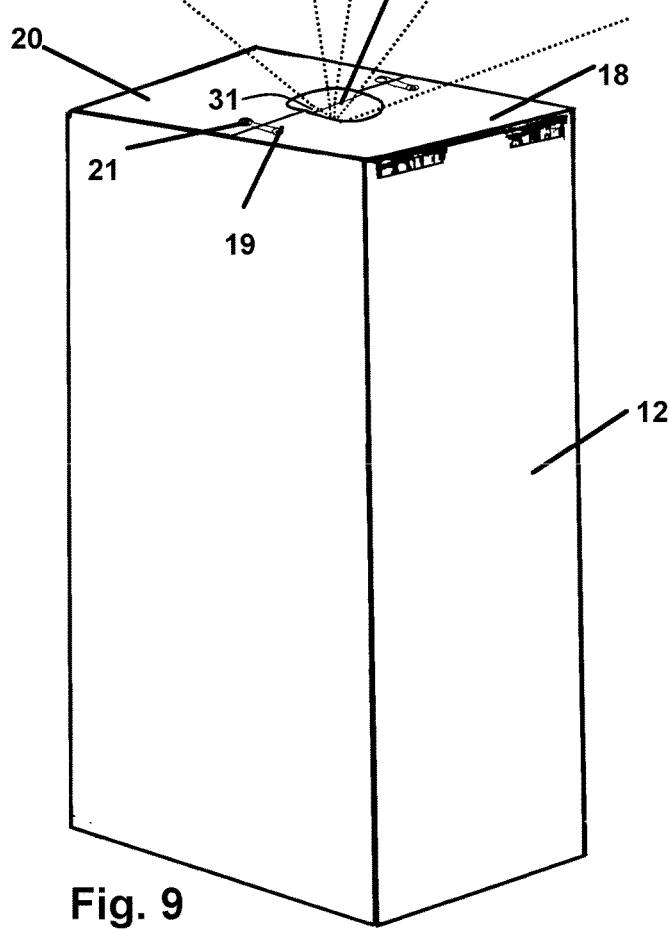
FIG. 9 depicts the device as in FIG. 1 showing an aperture formed with the overlapping flaps providing access to the bottle on the interior which can emit light and/or sound to gain the attention of the presence of the condom positioned in a mount.

Finally, FIG. 9 depicts the device 10 engaged to the product held in the container 12, such as in FIG. 1 where the first end 18 or flap, is closed and has a distal end slightly overlapping the distal end of the second end 20 or flap. Additionally shown is an aperture 45 communicating through the closed ends or flaps which must be opened to access the bottle 13 or product on the interior. Placement of the aperture 45 is in a registered positioning in line with and adjacent to the mount 16, such as in FIG. 5. In this mode, light and/or sound emitted from the mount 16 such as that of FIG. 5, gains the attention and gaze of the recipient from a distance and while opening the container 12, alerting them of the presence of the mount 16 and the condom 22.

While all of the fundamental characteristics and features of the invention have been shown and described herein, with reference to particular embodiments thereof, a latitude of modification, various changes and substitutions are intended in the foregoing disclosure and it will be apparent that, in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. A packaging apparatus for placement of condoms in a gaze-attracting position to a recipient of a gift or product, comprising:

a mount having a body having a first side adapted for an engagement at an engagement position upon a product;

said mount having a second side holding a condom in a removable engagement;

said body of said mount adapted to engage upon a said product which is a bottle by a sleeve extending from said first side of said body of said mount; and said sleeve having an axial opening having a diameter sized to slide upon and surround a dispensing end of said bottle, wherein said mount must be removed by disengagement of said sleeve from said dispensing end of said bottle, in order to dispense liquid therefrom and whereby the gaze of a recipient receiving said product, is attracted to said engagement position upon opening said product or opening packaging surrounding said product, whereupon the presence of said condom in said mount is easily ascertained.

2. A packaging apparatus for placement of condoms in a gaze-attracting position to a recipient of a product, comprising:

a mount having a body having a first side adapted for an engagement at an engagement position upon a product or upon an openable end of packaging surrounding said product;

said mount having a second side holding a condom in a removable engagement;

said packaging being a box having said openable end communicating with an interior cavity;

said openable end sealed by a first flap, in contact with and covering an overlap portion of an underlying second flap;

mating fasteners to hold said first flap covering said overlap portion of said second flap; and said openable end accessible only by first folding a first flap in a direction away from said second flap and subsequently folding said second flap in a direction away from said first flap whereby the gaze of a recipient receiving said product, is attracted to said engagement position upon opening said packaging surrounding said product, whereupon the presence of said condom in said mount is easily ascertained.

3. The packaging apparatus of claim 1, additionally comprising:

said packaging being a box having an openable end communicating with an interior cavity;

said openable end sealed by a first flap, in contact with and covering an overlap portion of an underlying second flap;

mating fasteners to hold said first flap covering said overlap portion of said second flap; and said openable end accessible only by first folding a first flap in a direction away from said second flap and subsequently folding said second flap in a direction away from said first flap.

4. The packaging apparatus of claim 2, additionally comprising:

said body engaged within said interior cavity to a sidewall of said box adjacent to a folding connection of said second flap, to said box.

5. A packaging apparatus for placement of condoms in a gaze-attracting position to a recipient of a gift or product, comprising:

a mount having a body having a first side adapted for an engagement at an engagement position upon a product or packaging surrounding said product;

said mount having a second side holding a condom in a removable engagement;

said removable engagement of said condom with said second side of said body is a slot;

a first portion of said condom engaged through said slot for a distance to a contact with a base of said body; and said distance from said slot to said base of said body being less than a total distance of an exterior of said condom whereby a portion of said condom extends above said slot thereby forming a grasping portion for said condom for removal from said slot and whereby the gaze of a recipient receiving said product, is attracted to said engagement position upon opening said product or packaging surrounding said product, whereupon the presence of said condom extending from said slot of said mount is easily ascertained.

6. The packaging apparatus of claim 1 additionally comprising:

said removable engagement of said condom with said first side of said body is a slot;

a first portion of said condom engaged through said slot for a distance to a contact with a base of said body; and said distance from said slot to said base of said body being less than a total distance of an exterior of said condom whereby a portion of said condom extends above said slot thereby forming a grasping portion for said condom for removal from said slot.

7. The packaging apparatus of claim 2 additionally comprising:

said removable engagement of said condom with said first side of said body is a slot;

a first portion of said condom engaged through said slot for a distance to a contact with a base of said body; and said distance from said slot to said base of said body being less than a total distance of an exterior of said condom whereby a portion of said condom extends above said slot thereby forming a grasping portion for said condom for removal from said slot.

8. The packaging apparatus of claim 3 additionally comprising:

said removable engagement of said condom with said first side of said body is a slot;

a first portion of said condom engaged through said slot for a distance to a contact with a base of said body; and said distance from said slot to said base of said body being less than a total distance of an exterior of said condom whereby a portion of said condom extends above said slot thereby forming a grasping portion for said condom for removal from said slot.

9. The packaging apparatus of claim 5 additionally comprising:

a light emitter engaged with said mount.

10. The packaging apparatus of claim 6 additionally comprising:

a light emitter engaged with said mount.

11. The packaging apparatus of claim 7 additionally comprising:

a light emitter engaged with said mount.

12. The packaging apparatus of claim 8 additionally comprising:

a light emitter engaged with said mount.

13. The packaging apparatus of claim 10 additionally comprising:

a sound emitter engaged with said mount.

14. The packaging apparatus of claim 11 additionally comprising:

a sound emitter engaged with said mount.

15. The packaging apparatus of claim 12 additionally comprising:

a sound emitter engaged with said mount.

* * * * *